US00PP32330P2

(12) United States Plant Patent
Hansen

(10) Patent No.: US PP32,330 P2
(45) Date of Patent: Oct. 13, 2020

(54) **X *MANGAVE* PLANT NAMED 'DESERT DAWN'**

(50) Latin Name: ***Agave* times x *Mangave* hybrid**
Varietal Denomination: Desert Dawn

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/602,323

(22) Filed: Sep. 13, 2019

(51) Int. Cl.
*A01H 5/12* (2018.01)
*A01H 6/12* (2018.01)

(52) U.S. Cl.
USPC ..... Plt./373

(58) Field of Classification Search
USPC ..... Plt./373
CPC ... A01H 5/12; A01H 5/02; A01H 5/00; A01H 6/12; A01H 1/02
See application file for complete search history.

(56) References Cited

U.S. PATENT DOCUMENTS

PP30,904 P2 * 9/2019 Hansen ..... A01H 5/12 Plt./373
PP31,251 P2 * 12/2019 Hansen ..... A01H 5/12 Plt./373
PP31,274 P2 * 12/2019 Hansen ..... A01H 5/12 Plt./373
PP31,459 P2 * 2/2020 Hansen ..... A01H 5/12 Plt./373
PP31,601 P2 * 3/2020 Hansen ..... A01H 6/12 Plt./373
PP31,630 P2 * 3/2020 Hansen ..... A01H 6/12 Plt./373

OTHER PUBLICATIONS

Bock's Blog Succulents and More New Hans Hansen xMangave releases for 2019, retrieved on Apr. 2, 2020, retrieved from the Internet at https://www.succulentsandmore.com/2019/02/new-hans-hansen-mangave-releases-for.html, 11 pp. (Year: 2019).*

* cited by examiner

*Primary Examiner* — June Hwu

(57) ABSTRACT

A new and unique x *Mangave* plant named 'Desert Dawn' characterized by a rounded mound of fleshy, fleshy, linear to lanceolate leaves that develop dense reddish to greyed reddish-purple spotting with intense light and is proximally outwardly with slightly upwardly toward apex. The leaves have numerous small, firm marginal teeth pointing outwardly to slightly recurving toward base. The upper foliage develops a distinct purplish center stripe. The new plant is suitable for the garden or as a potted plant in the garden or home.

1 Drawing Sheet

Botanical classification: *Agave* times x *Mangave* hybrid. Variety denomination: 'Desert Dawn'.

STATEMENT REGARDING PRIOR DISCLOSURES UNDER 37 CFR 1.77(B)(6)

The first disclosure of the claimed plant, in the form of a private sale, was made by Walters Gardens, Inc. on Oct. 15, 2018 to Plant Delights Nursery, Inc. The first non-enabling public disclosure of x *Mangave* 'Desert Dawn' was early in 2019 as a brief description and photo on a website operated by Plant Delights Nursery, Inc. Information for this website and plants for this sale were obtained from the inventor. No plants of x *Mangave* 'Desert Dawn' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Desert Dawn' that was hybridized by the inventor at a wholesale perennial nursery in Zeeland, Mich., USA as a cross between a proprietary unnamed selection of *Agave nizandensis* (not patented) as the female or seed parent times and x *Mangave* 'Bloodspot' (not patented) as the male or pollen parent. The cross was performed Jul. 10, 2014 and seeds were harvested and sown later the following autumn. Through trials at the same nursery the plant was assigned the breeder code 14-171-5. The new plant has been successfully asexually propagated by sterile shoot-tip tissue culture and by basal offsets at the same nursery in Zeeland, Mich. The asexual tissue culture propagation has been found to produce stable and identical plants that maintain all the unique characteristics of the original plant.

BRIEF SUMMARY OF THE INVENTION x *Mangave* 'Desert Dawn' differs from its parents as well as all other *Manfreda, Agave* and x *Mangave* known to the applicant. The female parent has a flatter habit with fewer leaves per plant, with narrow, dark green leaves, longer, arching foliage that has small marginal teeth, moderately channeled or concavo-convex with a lighter chartreuse in the center along midrib rather than the purple center of the new plant, and the leaves of the female do not have reddish-purple spots or central purple stipe. The male parent is more upright in habit with foliage that is shorter, more glaucous, more numerous, thicker (abaxial to adaxial), dark brown around the marginal teeth and larger terminal spines and larger, more-pronounced mahogany spots and lacks the purple center strip down the middle of the leaves. The nearest comparison plants are: 'Painted Desert' U.S. Plant Pat. No. 31,630, 'Blazing Saddles' U.S. Plant Pat. No. 31,274, 'Racing Stripes' U.S. Plant Pat. No. 30,904, 'Frosted Elegance' copending U.S. Plant patent application Ser. No. 16/602,324, 'Red Wing' U.S. Plant Pat. No. 31,459, 'Freckles and Speckles' U.S. Plant Pat. No. 30,904, 'Shadow Waltz' U.S. Plant Pat. No. 31,601 and 'Mission to Mars' U.S. Plant Pat. No. 29,393. 'Racing Stripes' is a taller plant with slightly broader leaves that have a dark green margins, chartreuse-yellow in the center band and no reddish coloration. 'Painted Desert' has a flatter habit with foliage that is less completely spotted with greyed-purple and has a lighter chartreuse center stripe with greyed purple spotting, the marginal teeth are smaller, lighter colored and more flexible. 'Frosted Elegance' has a smaller more compact habit with foliage that is bluish-green with a lighter colored stripe down the leaf center. 'Red Wing' has broader leaves and the reddish coloration is more of cherry-red without the distinct purple stripe down the leaf center. 'Freckles and Speckles' has more arching foliage with spots that are more separated, lacks both the intense grey-purple and the center purple stripe. 'Shadow Waltz' has leaves with broad dark green margin and light green to chartreuse center. 'Mission to Mars' is a much larger plant with longer and broader foliage of more uniform burgundy coloration.

'Desert Dawn' is unique from all of the above cultivars and all *Agave*, x *Mangave* and *Manfreda* known to the inventor by the following combined traits:

1. Rounded mound of linear to lanceolate sarcous leaves;
2. Leaves develop dense greyed reddish-purple coloration with strong ultraviolet light;
3. Leaf margins have many, small, sharp, firm, outward to slightly-recurved, marginal teeth;
4. Leaf upper surface has distinct purplish centers.
5. Moderate growth rate;
6. Foliage is outwardly with distal portion slightly upwardly.

BRIEF DESCRIPTION OF THE DRAWING

The photograph of x *Mangave* 'Desert Dawn' demonstrates the overall appearance of the new plant including the unique traits as four-year-old plants grown in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
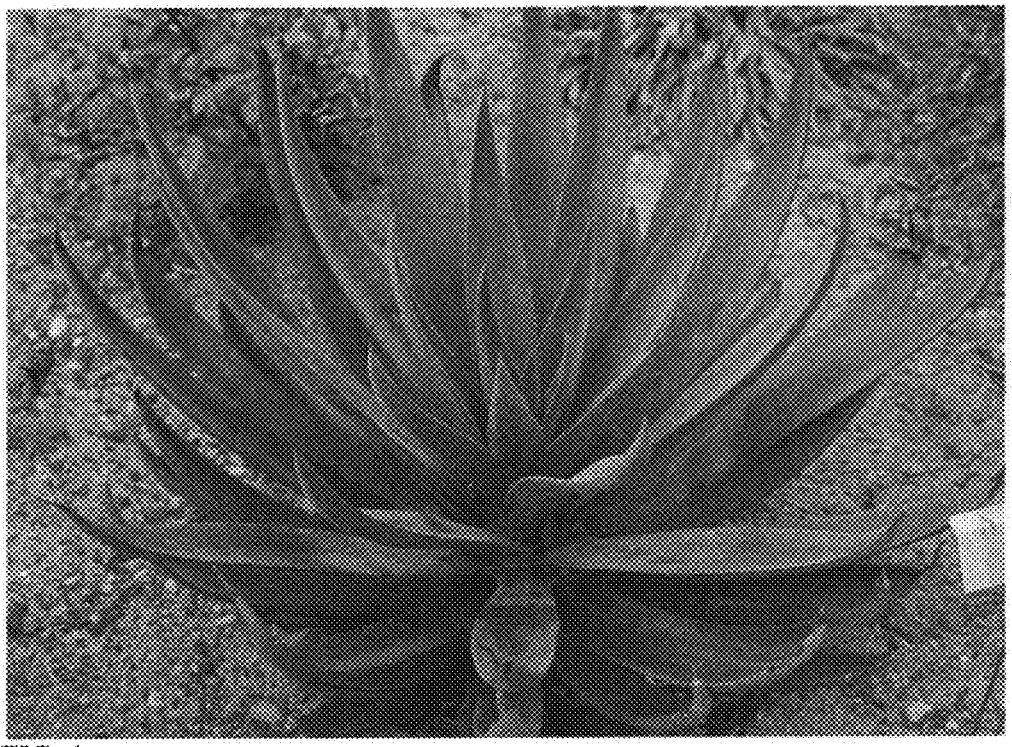
FIG. 1 shows a side view of a greenhouse grown plant that was grown in full-sun for the most recent season.
Figure 2:
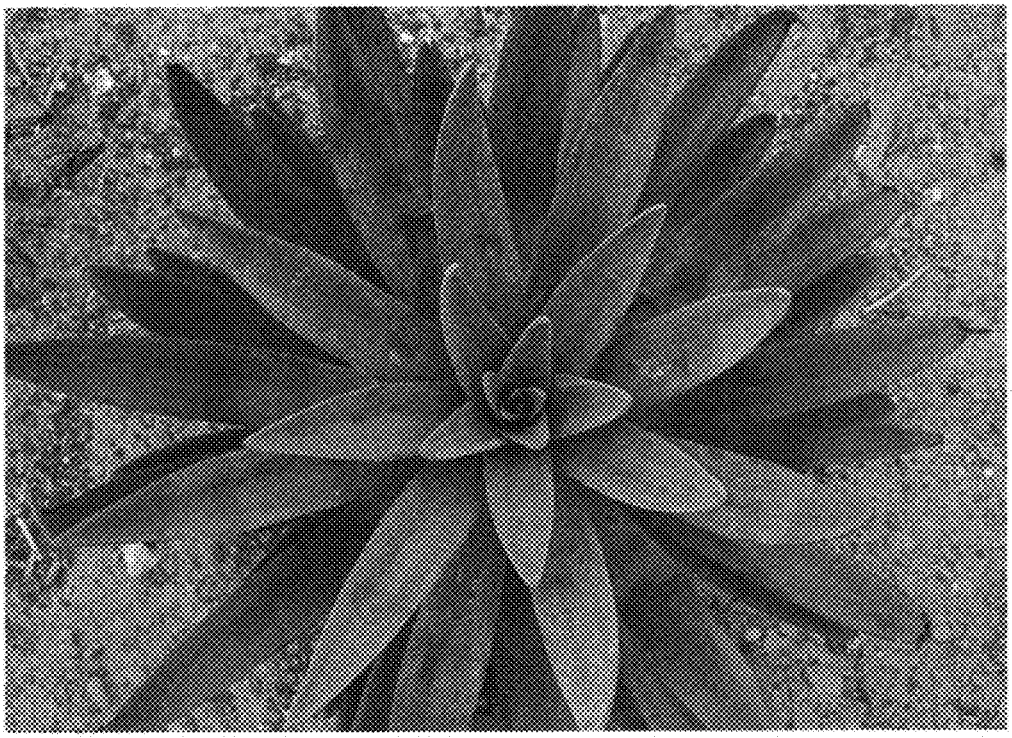
FIG. 2 shows top view of a greenhouse grown that was grown in full-sun for the most recent season.

The following descriptions and color references are based on the 2015 edition of The Royal Horticultural Society Colour Chart except where common dictionary terms are used. The new plant, x *Mangave* 'Desert Dawn', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse in Zeeland, Mich. with supplemental water and fertilizer as needed.

Parentage: A proprietary unnamed selection of *Agave nizandensis* as female or seed patent and x *Mangave* 'Bloodspot' as the male or pollen parent;

Propagation: By sterile shoot-tip tissue culture and removal of basal offsets;

Time to initiate roots from tissue culture: About 21 days;

Growth rate: Moderate;

Crop time: About 14 to 18 weeks to finish in a 3.8 liter container from a 35 mm tissue culture growing at about 21° C.;

Rooting habit: Fleshy, lightly branching, with roots up to 30 cm long;

Root color: Nearest RHS NN155B;

Plant shape and habit: Succulent herbaceous perennial with basal rosettes of about 76 leaves radially emerging outwardly from central stem and then curving slightly upwardly in distal portion, producing a radially-symmetrical, rounded mound;

Plant size: Foliage height about 38.0 cm tall from soil line to the top of the leaves and about 47.0 cm wide at the widest point about 15 cm above soil level;

Stem: To about 5.0 cm across; covered with leaves;

Foliage description: Linear to lanceolate; simple; sessile; bi-laterally symmetrical; sarcous; apex narrowly acute with firm terminal spine; base truncate; flat proximally to slightly concavo-convex distally; margins flat; margins finely serrate with small, firm, outwardly to slightly recurved facing teeth; glabrous abaxial and adaxial; matte abaxial and adaxial;

Apical spine size: To about 11.0 mm long and 1.0 mm wide at base;

Marginal teeth size: Firm and sharp; about 1.0 mm long and 2.0 mm wide at base, average spacing about 1.8 mm apart;

Leaf size: To about 33.0 cm long, about 42.0 mm wide toward middle; center base about 11.0 mm thick at basal midrib; average about 28.0 cm long, 38.0 mm wide and 10.0 mm thick in longitudinal center near base; mottled to maculate adaxial and abaxial with spots of variable sizes from 1.0 mm to 5.0 mm across;

Foliage fragrance: None observed;

Leaf number: About 76 per plant;

Leaf blade color:

*Adaxial* (*low light*).—Margins between RHS N138B and RHS 191B with spots between RHS 187A and RHS N187A and center nearest blend between RHS N187B and RHS 79B.

*Abaxial* (*low light*).—Margins and centers nearest blend between RHS N138A and RHS 189B.

*Adaxial* (*high light*).—Longitudinal center 8.0 to 12.0 mm wide blend of nearest RHS N186C and RHS N187A, marginally nearest RHS N187A with small green patches nearest RHS 137A of about 1.0 mm diameter, becoming nearest RHS N187A distally with highest light intensity.

*Abaxial* (*high light*).—Small, irregular, green mottled patches of variable size between 1.0 and 5.0 mm across, nearest RHS 137B on a blend between RHS N187A and RHS 137B.

*Teeth*.—Variable with maturity; on young developing leaves nearest RHS 163B, on semi-mature leaves nearest RHS 166B, on mature leaves nearest RHS 166A.

*Terminal spine*.—On young developing leaves nearest RHS 171A, on mature leaves between RHS 200A and RHS 202A.

Petiole: Leaves sessile;

Veins: Parallel; not distinct abaxial or adaxial;

Flower description: Not yet observed;

Fruit and seed not observed;

Disease resistance: x *Mangave* 'Desert Dawn' has not been observed to be resistant to diseases beyond that which is normal for x *Mangave, Agave* or *Manfreda*. The new plant is xeromorphic and survives well with minimal water once established. The new plant is estimated to be hardy at least from USDA zone 9. Full extent of winter hardiness has not been tested.

It is claimed:

1. A new and distinct cultivar of ornamental x *Mangave* plant named 'Desert Dawn' as herein described and illustrated.

* * * * *